United States Patent [19]

Gorshkov et al.

[11] Patent Number: 5,197,980
[45] Date of Patent: Mar. 30, 1993

[54] CARDIAC VALVE PROSTHESIS

[76] Inventors: Jury V. Gorshkov, prospekt Mira, 17, kv. 9; Sergei V. Evdokimov, ulitsa Chepetskaya, 20, kv. 70; Alexandr P. Melnikov, ulitsa Sosnovaya, 22, korpus 2, kv. 54, all of Kirovo-Chepetsk, Kirovskaya oblast,, U.S.S.R.

[21] Appl. No.: 744,329

[22] Filed: Aug. 13, 1991

[30] Foreign Application Priority Data

Aug. 14, 1990 [SU] U.S.S.R. ............... 4858589

[51] Int. Cl.$^5$ .................................. A61F 2/24
[52] U.S. Cl. ........................ 623/2; 137/512.1; 137/527
[58] Field of Search ............ 623/2; 137/512.1, 527, 137/527.8

[56] References Cited

U.S. PATENT DOCUMENTS

| 4,274,437 | 6/1981 | Watts | 623/2 |
| 4,689,046 | 8/1987 | Bokros | 623/2 |

FOREIGN PATENT DOCUMENTS

| 0403649 | 12/1990 | European Pat. Off. | |
| 1572602 | 6/1990 | U.S.S.R. | 623/2 |

Primary Examiner—Ronald Frinks
Attorney, Agent, or Firm—Lilling & Lilling

[57] ABSTRACT

A cardiac valve prosthesis comprising an annular body housing a closure member in the form of two cusps. The cusps open and close freely and rotate simultaneously around the body axis, checking the forward and reverse blood flows through the prosthesis to simulate the operation of the cardiac valve. To have the operation of the prosthesis resemble that of the natural valve, the lateral surface of at least one cusp is provided with a recess to produce a controlled blood backflow through the prosthesis by causing the blood flow through the prosthesis to swirl.

6 Claims, 4 Drawing Sheets

CARDIAC VALVE PROSTHESIS

FIELD OF THE INVENTION

The invention relates to medical technology, and in particular to substitutes of natural valves of the human heart.

The present invention can be used most advantageously to replace the aortic and mitral cardiac valves. Besides, it can optionally be used as a substitute for the tricuspid valve or the pulmonary valve.

BACKGROUND OF THE INVENTION

The problem of developing cardiac valve prostheses, capable of replacing in a satisfactory manner the natural valves of the human heart to correct their dysfunction due to congenital or acquired pathology, has a more than thirty-year history.

Over these decades, a vast number of valve prosthesis designs have been developed and used in practice. Generally, such a prosthesis comprises a return valve permitting forward blood flow in the open position of the closure member and preventing the reverse blood flow in the closed position of the closure member.

Owing to their superb hemodynamic characteristics ensuring a central and virtually laminar flow, the cardiological science has accepted for wide-scale application cardiac valve prostheses, in which the closure member is designed in the form of two semicircular cusps pivoted to the prosthesis body.

Known in the art is a cardiac valve prosthesis (ref. U.S. Pat. No. 4,689,046) which comprises an annular body, the inner surface of which defines a central opening for the passage of the forward blood flow. The annular body houses a closure member in the form of two cusps which pivot from the open position and back. A cusp has an ascending surface at the side of the ascending flow and a descending surface at the side of the descending flow, and also a lateral surface contacting the inner surface of the annular body in the closed position. The annular body is provided on the inner surface thereof with spaced recesses engageable by the projections of the cusps provided on the opposite sides of the lateral surfaces.

During operation of the aforesaid cardiac valve prosthesis, the cusps of the closure member do not alter their position relative to the body axis depending on a particular cardiac cycle moment, i.e., either in the closed position, or in the open position, or in the intermediate position. This situation causes the appearance of blood congestion zones which stimulate thrombus forming processes that lead to either a thrombosis of the prosthetic valve or thromboembolic complications. Furthermore, the local wear of individual portions of the annular body and cusps of the closure member, which cooperate constantly or cyclically with one another, reduces the service life of the cardiac valve prosthesis.

An attempt to overcome the above-mentioned drawbacks was made in a cardiac valve prosthesis described, for example, in U.S. Pat. No. 4,274,437. This prosthesis comprises an annular body having an inner surface defining an opening for the forward blood flow along the body axis and two valve members complementing each other and secured inside the body to prevent the backflow of blood in the closed position. The annular body is provided with a slot extending along the entire circumferential length of its inner surface and receiving projections provided on the opposite sides of each valve member to allow the valve members to turn from the closed to the open position and back. Each of the valve members has an outer convex surface and an ascending portion having a semicircular outer edge. The edge contacts the inner surface of the annular body and checks the backflow of blood in the closed position of the prosthesis. In addition to the turning movement from the closed to the open position and back, the valve members of this prosthesis can partially rotate about the axis of the annular body, thereby preventing the development of congestion zones and reducing the wear of the cooperating components of the prosthesis.

One of the drawbacks of this cardiac valve prosthesis is that it lacks means for producing the rotation about the body axis. The rotation can be generated in this prosthesis only by the fluctuating swirling in the blood flowing through the valve prosthesis. Obviously, the rotation of the valve members due to random flow irregularities would be chaotic and impossible to control in order to produce a positive effect. The relatively high profile of the cardiac valve further reduces the positive effect, because the cardiac structures surrounding the prosthesis inhibit the rotation of the valve members.

In the inventors' view, the most successful design is the cardiac valve prosthesis disclosed in European Application No. PCT/SU 88/00258. The cardiac valve prosthesis comprises an annular body having an inner surface that defines an opening for the forward blood flow, and a closure member received in the annular body and designed in the form of two cusps having an ascending and a descending surfaces and a lateral surface confined therebetween and contacting the inner surface of the annular body in the closed position to check the backflow of blood.

The annular body has a projection extending along the entire circumference of the inner surface thereof to engage slots provided on the opposite sides of the lateral surface of each cusp. Each cusp is provided with a detent to maintain a desired spacing between the cusps in the open position. The slot provided on each of the opposite sides of the lateral surface of the cusp is an open-ended groove. The profile of the lateral sides of the slot is a broken line having a first and a second portions. The like portions of the broken lines of the lateral sides of the slots on the opposite sides of the lateral surface of the cusp have different lengths.

Following below is a detailed description of the closing moment of one of the cusps of the aforesaid cardiac valve prosthesis. The excess pressure of the backflow of blood acting upon a cusp causes the latter to turn into a closed position as it bears along the intersection line of the broken lateral side of the slot against the surface of the projection provided on the inner surface of the annular body. In this case, since the like portions of the broken lines have different lengths the opposite sides of the lateral surface of the cusp move to a different distance relative to the inner surface of the annular body. This causes the cusp to turn about the axis of the annular body.

It follows from the above description of the operation of the cardiac valve prosthesis that the mechanism causing rotation of the cusps about the body axis is based on the difference in the forces of friction resulting from the interaction between the lateral side surface of the cusp slot and the projection on the inner surface of the annular body. To allow long-term faultless operation, antifriction materials, for example, pyrolytic carbon, are used as the material of the prosthesis components. As a result, the aforesaid friction forces are very small. Therefore, the rotation of the cusps about the body axis would be greatly influenced by various fluctuation processes occurring in the forward and reverse blood flows through the prosthesis. These flows produce chaotic movement, thereby minimizing the effect of the cardiac valve prosthesis.

Besides, the small thickness of the cusp makes for a small difference in the length of the broken line portions of the slots on the opposite sides of the cusps, thereby obviating the possibility of the cusps rotating at a sufficiently high speed about the body axis which, in turn, prevents blood flow swirling essential for normal operation of the heart.

SUMMARY OF THE INVENTION

It is an object of the present invention to develop a cardiac valve prosthesis which is designed to produce additional back swirling of the blood flows forcing the cusps to turn about the body axis and to flush intensively the prosthesis components by the forward and reverse blood flows, thereby effectively improving resistance to thrombus formation.

Another object of the invention is to improve the hemodynamic characteristics of the cardiac valve prosthesis.

A further object of the invention is to extend the service life of the cardiac valve prosthesis.

These objects are achieved by a cardiac valve prosthesis comprising an annular body having an inner surface which defines a passage for the direct blood flow along the axis of the body, and containing a closure member consisting of two cusps having an ascending surface facing the ascending forward blood flow and a descending surface facing the descending reverse blood flow, and lateral surfaces which are surfaces of revolution contacting the inner surface of the annular body in the closed position of the prosthesis to check the reverse blood flow. The cusps are secured inside the body to turn from the closed position into the open position and back by means of a device comprising two engageable members, one of which extends along the entire circumferential length of the inner surface of the body, and the other is provided on the opposite sides of the lateral surface of each cusp. According to the invention, the lateral surface of at least one cusp is provided with a recess to produce a controlled reverse blood flow through the prosthesis. This reverse blood flow produces a cyclic torque causing a slow rotation of the cusps about the body axis.

It is preferred that said two engageable members are a projection and a slot, the slot being provided on the body and the projection being provided on the opposite sides of the lateral surface of each cusp.

Alternatively, it is preferred that said two engageable members are a projection and a slot, the projection being provided on the body and the slot being provided on the opposite sides of the lateral surface of each cusp.

It is also preferred that the recess on the side surface of at least one cusp has a depth H and a width L related by the following formula:

$$H^3 \cdot L \leq 3 \cdot 10^{-13} (m^4).$$

It is further preferred that the recess on the lateral surface of the cusp should have a plane of symmetry inclined to the rotation axis of said lateral surface of the cusp.

The above objects are also attained by a cardiac valve prosthesis comprising an annular body having an inner surface which defines a passage for the forward blood flow along the axis of the body which houses a closure member consisting of two cusps having an ascending surface facing the ascendidng forward blood flow and a descending surface facing the descending reverse blood flow and lateral surfaces which are surfaces of revolution contacting the inner surface of the annular body in the closed position of the prosthesis. The cusps are secured inside the body for rotation from the closed position to the open position and back from a device comprising two engageable members, one of which extends along the entire circumferential length of the inner surface of the body and the other is provided on the opposite sides of the lateral surface of each cusp. According to the invention, the cusps are provided with detents in contact with one another, the height of which detents allows the blood flow in the open position of the cusps to be divided into three approximately equal portions.

Apart from its advantageously small size, the present cardiac valve prosthesis has improved hemodynamic characteristics, preventing completely thrombus formation, and its service life is extended as a result of the cusps being forced to rotate about the prosthesis axis. Moreover, the torque imparting rotation to the cusps is generated by the design of the prosthesis components. By changing the structural parameters, it is possible to achieve a desired rotation speed of the cusps about the body axis.

BRIEF DESCRIPTION OF THE INVENTION

The invention is further explained in the following description of a specific embodiment thereof with reference to the accompanying drawings, wherein.

BEST MODE OF CARRYING OUT THE INVENTION

Figure 1:
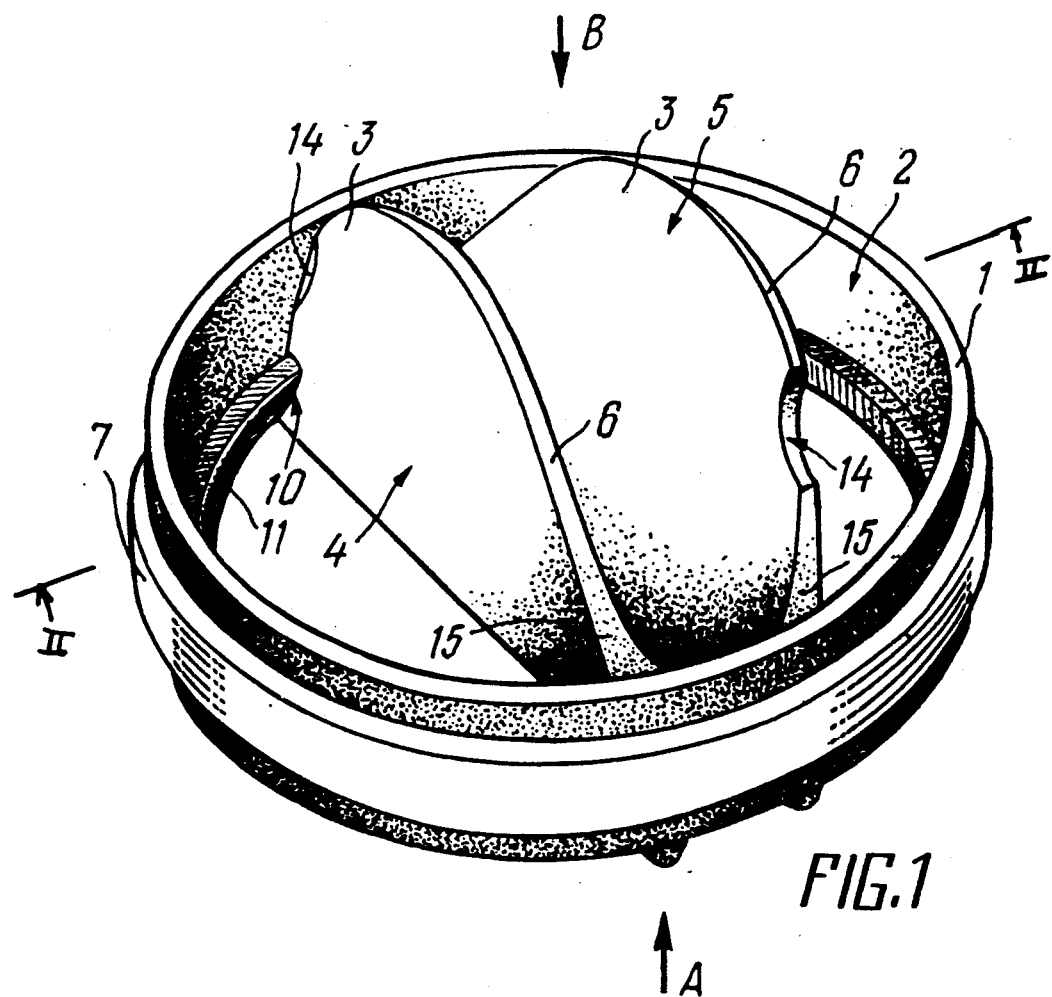
FIG. 1 is a general view of a cardiac valve prosthesis according to the invention.

The present cardiac valve prosthesis comprises an annular body 1 (FIG. 1). An inner surface 2 of the body 1 defines a passage for the forward blood flow shown by an arrow A along the axis of the body 1. The body 1 houses a closure member in the form of two cusps 3.

Each of the cusps 3 has an ascending surface 4 facing the ascending forward blood flow and a descending surface 5 facing the descending reverse blood flow shown by an arrow B.

Lateral surfaces 6 of the cusps 3 are surfaces of revolution contacting the inner surface 2 of the annular body 1 in the closed position of the prosthesis, checking the reverse blood flow B.

Figure 2:
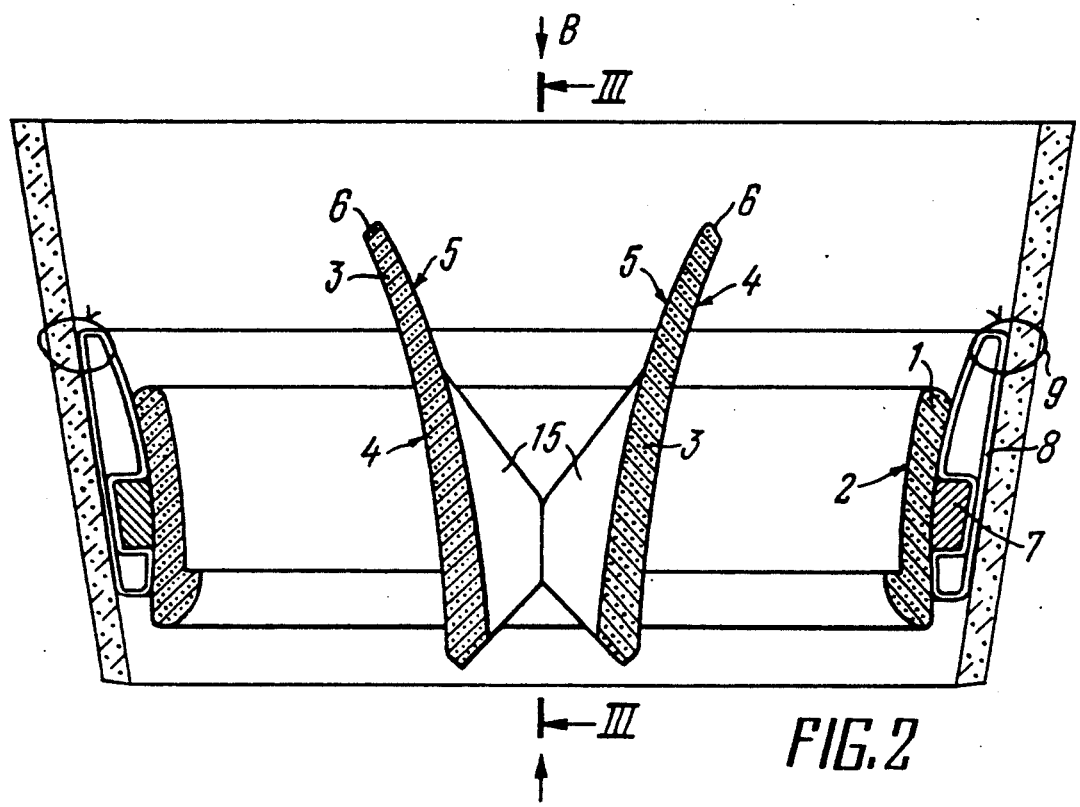
FIG. 2 is a sectional view of the cardiac valve prosthesis along the line II—II in FIG. 1, provided with a cuff secured in a cardial vessel, according to the invention.

The outer surface of the body 1 is provided with a stiffness ring 7 having a cuff 8 fitted thereon (FIG. 2) to allow the prosthesis to be grafted into the cardiac tissue, by non-absorbable suture 9.

The body 1 and the cusps 3 of the prosthesis can be made of any biocompatible anti-thrombogenic and wear-resistant material, for example, pyrolytic carbon. The stiffness ring 7, too, is made of a biocompatible material having a high modulus of elasticity, for example, an alloy based on cobalt and molybdenum. The cuff 8 is preferably made of a biocompatible material allowing rapid implantation of the prosthesis.

Figure 3:
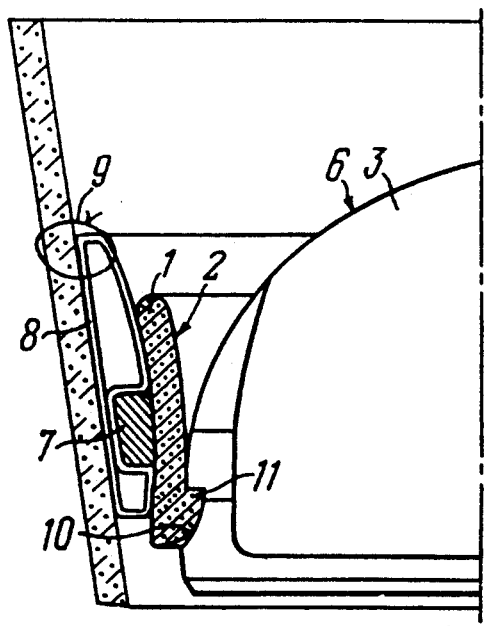
FIG. 3 is a partial sectional view along the line III—III in FIG. 2 (first embodiment), according to the invention.

The cusps 3 are secured inside the body 1 to be turned from the closed position to the open position and back by means of a device comprising two engageable members. In the embodiment described, the device is a slot 10 (FIG. 3) and a projection 11, the projection being provided on the inner surface 2 of the body 1 over the entire circumferential length and the slot 10 being provided on the opposite sides of each cusp 3, on the lateral surface 6 thereof.

Figure 4:
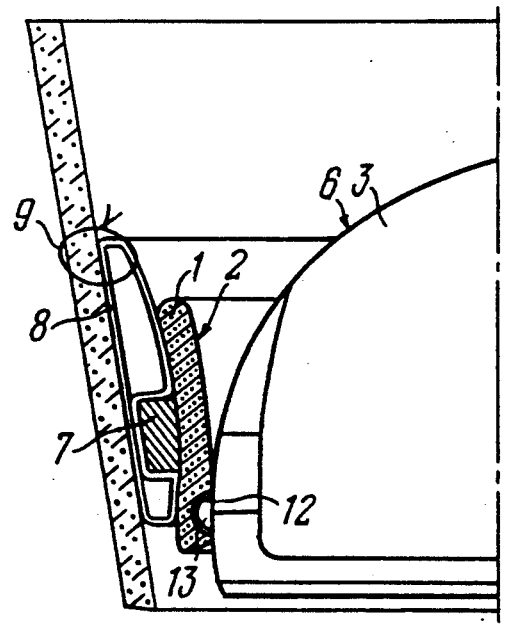
FIG. 4 is a partial sectional view along the line III—III in FIG. 2 (second embodiment), according to the invention.

In another embodiment of the device, the inner surface 2 (FIG. 4) of the body 1 is provided with a slot 12 extending along the entire circumferential length, and a projection 13 is provided on the opposite sides of each cusp 3, on the lateral surface thereof.

In the embodiment described, the lateral surface 6 (FIG. 1) of both cusps 3 is provided with a recess 14 which is designed to produce a controlled reverse blood flow through the prosthesis. This flow generates a cyclic torque that causes the cusps 3 to rotate about the axis of the body 1 and the blood flow to swirl.

Figure 5:
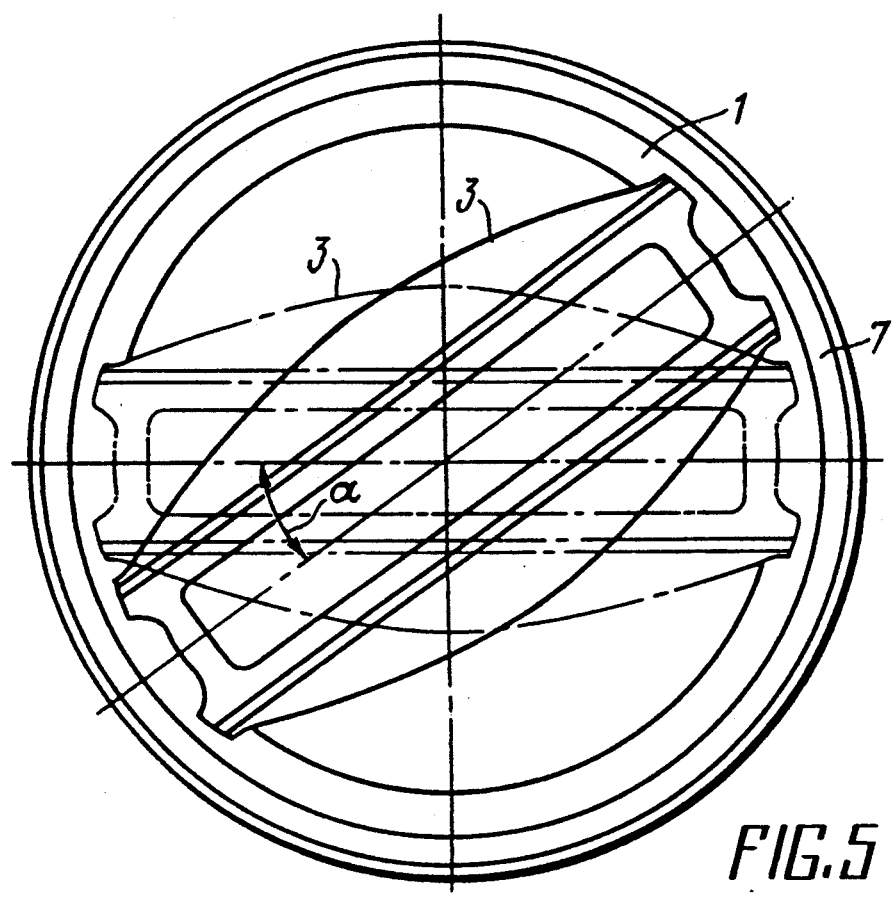
FIG. 5 is a bottom view of the prosthesis along the arrow A in FIG. 1, the dash lines showing the position of the cusps before they turn about the central axis of the body, according to the invention.

FIG. 5 shows a view of the cardiac valve prosthesis in the open position of the cusps at two different time moments. The cusps 3 are turned to an angle $\alpha$ about the central axis.

Said recess 14 (FIG. 6) has a depth H and a width L, which are related by the following formula:

$$H^3 \cdot L \leq 3 \cdot 10^{-13} (m^4).$$

Moreover, the symmetry plane C—C is inclined to the rotation axis d—d of the lateral surface 6 of the cusp 3 at an angle $\beta$.

The above formula was obtained at the following boundary conditions:

the forces acting upon the cusp are calculated at a time moment when the size of the slit between the lateral surface of the cusps and the inner surface of the body is comparable with the depth H of the recess 14 (in practice, H=0.02 to 0.04 mm);

the blood flow is stationary;

the recess has a constant width L and depth H; and the size of the slit between the lateral surface of the cusp and the inner surface of the body is identical along the perimeter of the inner surface of the valve body.

Because of the symmetry of the valve and the cusp, the distribution and magnitude of forces generated by evacuation in the wake of the blood moving through the slit between the inner surface of the body and the lateral surface of the cusp are identical over the entire perimeter of the slit, except for the forces in the recess of a depth H and a width L (a half valve with one cusp is considered here). By finding from the famous Bernoulli equation:

$$P_1 + \rho \cdot V^2/2 = \text{const} \quad (1)$$

wherein:

$P_1$ is the static pressure in the blood flow; and $\rho$ and V are the density and velocity of the blood flow, respectively, successively the flow velocity in the recess, the evacuation and the resultant force produced by said pressure and applied to the center of the recess, it is possible to determine the value of the moment Ms acting upon the cusps from the resultant force applied to the center of the recess and directed at right angles to the closure plane of the cusps:

$$M_s = [\rho \cdot \Delta P^2 \cdot H^4 \cdot L \cdot D \cdot \sin(2 \cdot \gamma)]/1152 \cdot \mu^2 \cdot b, \quad (\text{kg} \cdot \text{m/sec}^2) \cdot m, \quad (2)$$

wherein:

$\Delta P$ is the pressure difference across the valve;

H is the depth of the recess;

L is the width of the recess;

D is the diameter of the inner surface of the body $\gamma$ is the angle between the center of the recess and the closure plane of the cusps in a plane normal to the body axis;

$\mu$ is the dynamic viscosity of the liquid; and b is the thickness of the cusp edge.

As follows from the above, a recess provided on the lateral surface of at least one cusp helps produce an additional moment of forces that facilitates the forced turning of the cusps about the body axis, and, as follows from Formula (2), the magnitude of this moment depends on the structural parameters of the cusp (D, b), the operating conditions of the valve ($\rho$, $\mu$ and $\Delta P$) and parameters of the slot (H, L and $\gamma$).

To determine the values of H and L acceptable in practice, it is essential to take account of the regurgitation factor (backflow), the maximum value of which is normally accepted in practice to be equal to $Q_1 < = 20 \cdot 10^{-6} (m^3/\text{sec})$. A considerable increase in H and L would reduce the pressure tightness of the cardiac valve and cause the permissible values of the blood backflow (regurgitation) to be exceeded.

In accordance with the previously accepted approximation, the flow rate $Q_1$ through the recess can be evaluated from the formula:

$$Q_1 = \Delta P \cdot H^3 \cdot L / 12 \cdot \mu \cdot b, \ (m^3/\text{sec}). \quad (3)$$

A comparison of equations (2) and (3) shows that the value of the additional moment of forces Ms rises in proportion to the depth H of the recess in fourth power ($H^4$). The value of the backflow, however, also rises in proportion to the depth H of the recess in third power ($H^3$). The width L of the recess causes the value of both the additional torque and the value of the backflow increase in a linear manner. Therefore, an increase in the additional torque by increasing the depth of the depth H and width L of the recess is restricted by the growth of the backflow.

In view of the above requirements on the value of the blood backflow through the valve and by making essential substitutions in Equation (3) [for blood, $\mu = 3.5 \cdot 10^{-3}$ (kg/m·sec), $b = 3 \cdot 10^{-3}$ (m)—the maximum value used in practice], the following formula relating the depth H and width L of the recess is obtained:

$$H^3 \cdot L \leq 3 \cdot 10^{-13} (m^4).$$

The numerical assessment of the additional torque and backflow in the above-described embodiment of the invention has shown that the present invention helps produce an additional moment of forces sufficient to cause the cusps to turn about the body axis, for only an insignificant increase in the regurgitation volume, which is also confirmed by the results of visual observation of valve operation and the results of backflow determination in a test device.

Figure 7:
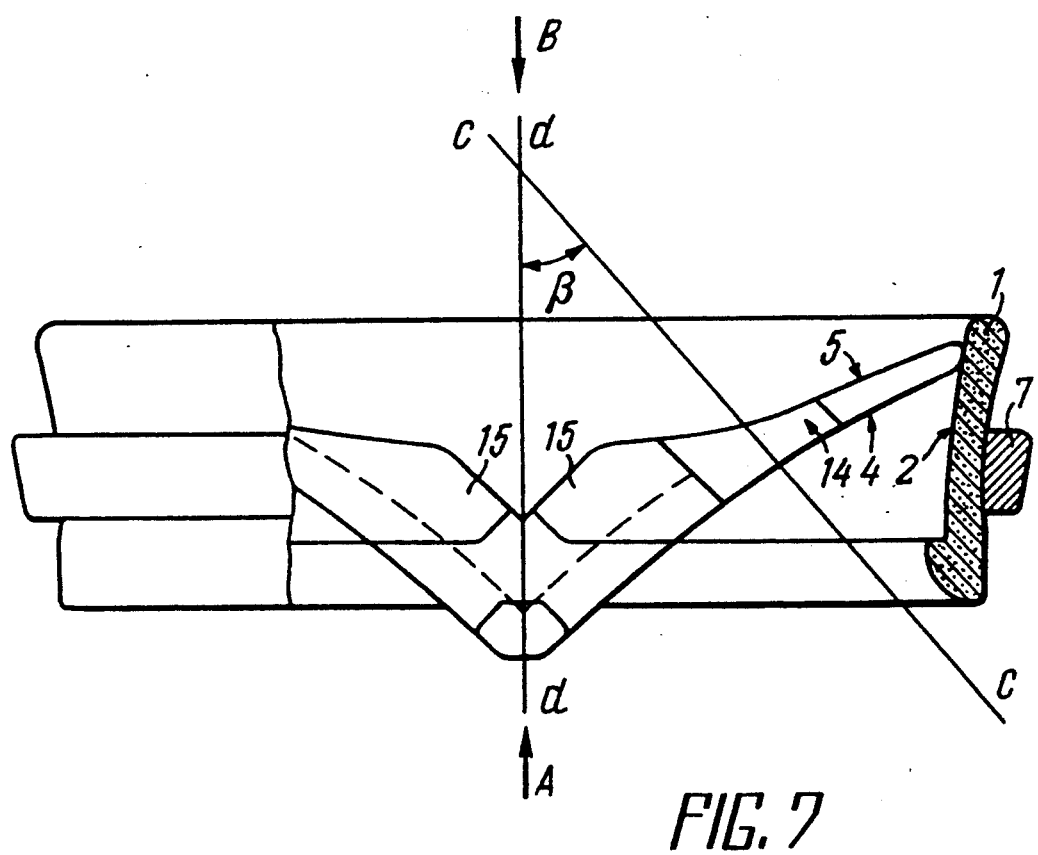
FIG. 7 is a partial sectional view of the cardiac valve prosthesis, the showing the cusps in the closed position, according to the invention.

The descending surfaces 5 of the cusps 3 are provided with detents 15 (FIGS. 1, 2 and 7) in contact with one another, the height of which ensures division of the blood flow into three approximately equal portions in the open position of the cusps 3.

The cardiac valve prosthesis operates as follows:

The method and technique for surgically implanting a cardiac valve prosthesis are not a subject matter of the present invention and are disclosed in numerous publications. It must be said only that the stiffness ring 7 provided on the outer surface of the body 1 and made of an alloy having a high modulus of elasticity helps prevent accidental deformation of the body 1 by the surgeon or the cardiac muscles upon pathological contractions.

The operation of the cardiac valve prosthesis is illustrated with reference to the aortic valve. Contraction of the ventricle produces a forward blood flow A (FIG. 1) into the aorta, under the effect of which the cusps 3 open, providing a passage for the blood flow through the cardiac valve prosthesis. The cusps 3 are opened as they turn about an imaginary axis extending through the slot 10 provided on the cusp 3. Furthermore, the engagement of the slot 10 of the cusp 3 and the projection 11 on the inner surface 2 of the body 1 permits free turning of the cusps 3.

In the open position of the cusps 3, the ascending surface 4, the descending surface 5 of the cusps 3 and the inner surface 2 of the body 1 are irrigated by the forward blood flow A. To reduce resistance to the forward blood flow A and to improve irrigation of the valve prosthesis surfaces with the blood flow, the inner surface 2 of the body 1 has the shape of a gradually flaring diffusor, and the cusps 3 are curved so that the ascending surface 4 has its concave side facing the ascending forward flow A.

Figure 6:
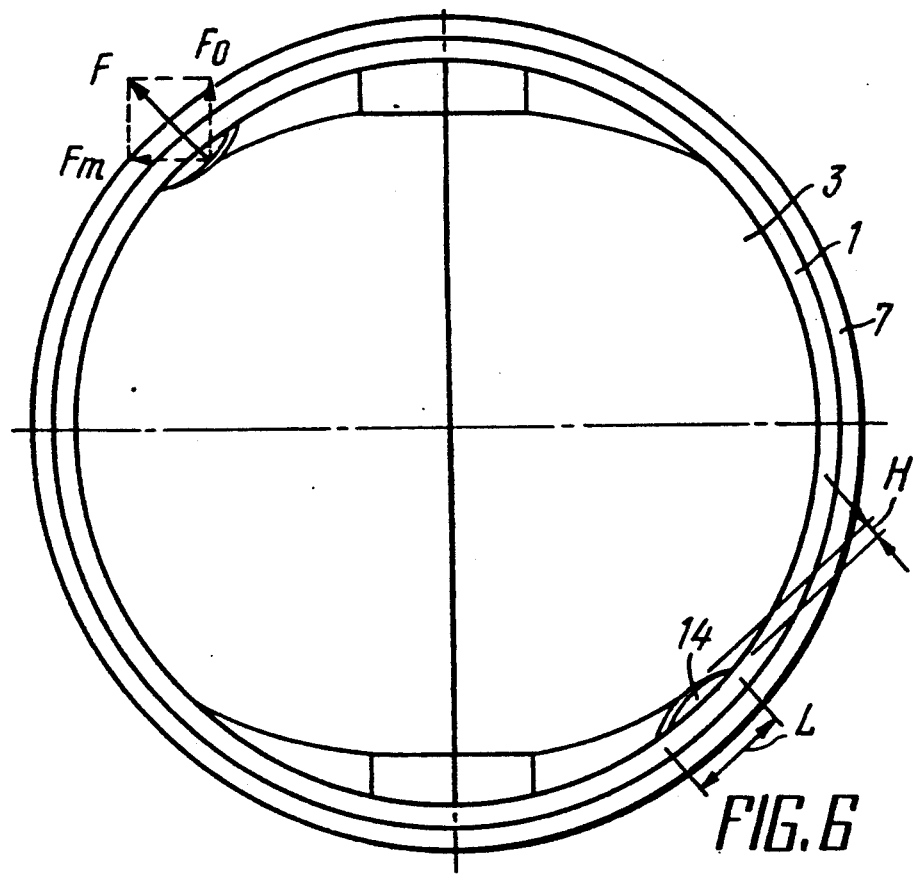
FIG. 6 is a top view of the prosthesis along the arrow B in FIG. 2, according to the invention but showing the cusps in a closed position.

During diastolic relaxation of the heart ventricle, the descendidng blood backflow B engages the cusps 3 of the cardiac valve prosthesis, causing them to close. Since the lateral surface 6 of the cusp 3 is provided with the recess 14, the velocity of the blood flow passing through the slit defined by the recess 14 and the inner surface 2 of the body 1 is higher than that of the blood flow passing through the slit defined by the lateral surface 6 of the cusp 3 and the inner surface 2 of the body 1. As a result, hydrodynamic forces F are generated (FIG. 6). The component of the force F, designated as $F_m$, is directed at right angles to the closure plane of the cusps 3 and produces a torque causing the cusps 3 to rotate about the axis of the body 1.

Furthermore, since the depth H of the recess 14 and its width 14 are related by the formula $H^3 \cdot L \leq 3 \cdot 10^{-13} (m^4)$, which is chosen to meet pressure tightness requirements of the valve, the use of the recess 14 does not cause considerable back blood leakage through the cardiac valve prosthesis.

In the closed position (FIG. 7), the lateral surface 6 of the cusps 3 adjoins the inner surface 2 of the body 1 and seals the free-passage opening of the body 1, thereby preventing the blood backflow B. A small portion of the blood backflow B leaks through the gaps between the projection 11 on the inner surface 2 of the body 1 and the slots 10 on the lateral surface 6 of the cusps 3, and through the recess 14. The inclination of the recess 14, that is, the inclination of the plane of symmetry C—C at an angle $\beta$ to the central axis of rotation of the lateral surface 6 of the cusp 3, allows the direction of the backflow B to be changed, that is swirled. This fact reduces the value of the blood backflow B and improves the irrigation of the surrounding cardiac tissues adjoining the prosthesis with the swirled backflow, thereby effectively reducing the risk of thrombus formation.

The rotation speed of the cusps 3 is adjusted by changing the value of the torque. The torque value rises in proportion to the depth H of the recess in fourth power, that is, $H^4$. However, the value of the backflow also rises in proportion to the depth H of the recess in third power, that is, $H^3$. The width L of the recess causes the torque and backflow to rise in a linear fashion. Therefore, an increase in the torque by increasing the depth H and width L of the recess is restricted by the blood backflow.

What is claimed is:

1. A cardiac valve prosthesis comprising:
   an annular body having an inner surface which defines a passage for the forward blood flow along the body axis;
   a closure member formed by first and second cusps, each of which has an ascending surface facing the ascending forward blood flow, a descending surface facing the descending blood backflow, and a lateral surface which serves as a surface of revolution and contacts said inner surface of said body in the closed position of the prosthesis to check said blood backflow;
   said first cusp and said second cusp secured inside said body to turn from the closed position to the open position and back by means of a device consisting of two engageable members;
   a first of said two engageable members of said device being provided on said inner surface of the body along the entire circumferential length thereof;
   a second of said two engageable members being provided on the opposite sides of said lateral surface of each said cusp; and
   a recess provided on said lateral surface of at least one said cusp to produce a controlled blood backflow through said cardiac valve prosthesis.

2. A cardiac valve prosthesis as claimed in claim 1, wherein said first of said two engageable members of said device is a projection, and said second of said two engageable members is a slot.

3. A cardiac valve prosthesis as claimed in claim 1, wherein said first of said two engageable members of said device is a slot, and said second of said two engageable members is a projection.

4. A cardiac valve prosthesis as claimed in claim 1, wherein said recess has a depth H and a width L related by the following formula:

$$H^3 \cdot L \leq 3 \cdot 10^{-13} (m^4).$$

5. A cardiac valve prosthesis as claimed in claim 1, wherein said recess has a plane of symmetry inclined at an angle $\alpha$ to said axis of rotation of said lateral surface of the cusp.

6. A cardiac valve prosthesis as claimed in any of the preceding claims 1 to 5, wherein each of said cusps is provided with a detent, said detents being in permanent contact with each other and having a height to divide said forward blood flow into three approximately equal portions in said open position of the valve.

* * * * *